(12) United States Patent
Kor-Sade et al.

(10) Patent No.: US 7,598,396 B2
(45) Date of Patent: Oct. 6, 2009

(54) CRYSTALLINE SOLIDS OF CARVEDILOL AND PROCESSES FOR THEIR PREPARATION

(75) Inventors: Ilan Kor-Sade, Shoham (IL); Shlomit Wizel, Petah Tiqva (IL)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 0 days.

(21) Appl. No.: 12/378,876

(22) Filed: Feb. 20, 2009

(65) Prior Publication Data

US 2009/0163721 A1 Jun. 25, 2009

Related U.S. Application Data

(62) Division of application No. 10/712,799, filed on Nov. 12, 2003, now Pat. No. 7,514,467, which is a division of application No. 10/342,905, filed on Jan. 15, 2003, now Pat. No. 6,710,184.

(60) Provisional application No. 60/349,310, filed on Jan. 15, 2002.

(51) Int. Cl.
C07D 209/82 (2006.01)

(52) U.S. Cl. ...................................... 548/440; 548/444

(58) Field of Classification Search ................. 548/440, 548/444
See application file for complete search history.

(56) References Cited

U.S. PATENT DOCUMENTS

| 4,503,067 | A | 3/1985 | Wiedemann et al. |
| 4,697,022 | A | 9/1987 | Leinert |
| 4,824,963 | A | 4/1989 | Leinert |
| 4,985,454 | A | 1/1991 | Leinert |
| 5,071,868 | A | 12/1991 | Leinert |
| 5,760,069 | A | 6/1998 | Lukas-Laskey et al. |
| 5,902,821 | A | 5/1999 | Lukas-Laskey et al. |
| 6,022,562 | A | 2/2000 | Autant et al. |
| 6,730,326 | B2 | 5/2004 | Beyer et al. |
| 6,777,559 | B2 | 8/2004 | Scalone et al. |
| 7,169,935 | B2 | 1/2007 | Scalone et al. |
| 2004/0127723 | A1 | 7/2004 | Scalone et al. |
| 2004/0198812 | A1 | 10/2004 | Bubendorf et al. |
| 2005/0240027 | A1 | 10/2005 | Brook et al. |
| 2005/0277689 | A1 | 12/2005 | Brook et al. |
| 2006/0148878 | A1 | 7/2006 | Bubendorf et al. |
| 2006/0167077 | A1 | 7/2006 | Hercek et al. |
| 2006/0270858 | A1 | 11/2006 | Chhabada et al. |
| 2007/0027202 | A1 | 2/2007 | Kumar et al. |
| 2007/0055069 | A1 | 3/2007 | Ramanjaneyulu et al. |
| 2007/0112054 | A1 | 5/2007 | Knipp et al. |
| 2007/0191456 | A1 | 8/2007 | Tarur et al. |
| 2007/0197797 | A1 | 8/2007 | Harrington |

FOREIGN PATENT DOCUMENTS

| EP | 0004920 | 10/1979 |
| EP | 0127099 | 12/1984 |
| EP | 0893440 | 1/1999 |
| EP | 0918055 | 5/1999 |
| KR | 1986-001761 | 10/1986 |
| WO | WO 99/05105 | 2/1999 |
| WO | WO 01/035938 | 5/2001 |
| WO | WO 03/005970 | 1/2003 |
| WO | WO 03/059807 | 7/2003 |
| WO | WO 2004/041783 | 5/2004 |
| WO | WO 2004/094378 | 11/2004 |
| WO | WO 2005/021504 | 3/2005 |
| WO | WO 2005/080329 | 9/2005 |
| WO | WO 2005/113502 | 12/2005 |
| WO | WO 2005/115981 | 12/2005 |
| WO | WO 2006/061364 | 6/2006 |
| WO | WO 2007/077111 | 7/2007 |
| WO | WO 2007/097504 | 8/2007 |

OTHER PUBLICATIONS

Chen et al., "Synthesis and Crystal Structure of Carvedilol", Jiegou Huaxue, vol. 17, No. 5, pp. 325-328 (1998).

*Primary Examiner*—Rebecca L Anderson
(74) *Attorney, Agent, or Firm*—Kenyon & Kenyon LLP

(57) ABSTRACT

This invention relates to a novel crystalline solid of carvedilol or a solvate thereof, to processes for its preparation, to compositions containing it and to its use in medicine. This invention further relates to a novel process for preparing a crystalline solid of carvedilol Form II.

6 Claims, 4 Drawing Sheets

CRYSTALLINE SOLIDS OF CARVEDILOL AND PROCESSES FOR THEIR PREPARATION

CROSS-REFERENCE TO RELATED APPLICATIONS

This application is a divisional of U.S. patent application Ser. No. 10/712,799, filed Nov. 12, 2003, now U.S. Pat. No. 7,514,467, which is a divisional of U.S. patent application Ser. No. 10/342,905, filed Jan. 15, 2003, now U.S. Pat. No. 6,710,184, which claims the benefit of U.S. Provisional Application No. 60/349,310, filed Jan. 15, 2002, which is incorporated herein by reference.

FIELD OF THE INVENTION

This invention relates to a novel crystalline solid of carvedilol or a solvate thereof, to processes for its preparation, to compositions containing it and to its use in medicine. This invention further relates to a novel process for preparing crystalline carvedilol Form II.

BACKGROUND OF THE INVENTION

Carvedilol, (±)-1-(Carbazol-4-yloxy)-3-[[2-(o-methoxyphenoxy)ethyl]amino]-2-propanol, is a nonselective β-adrenergic blocker with $\alpha_1$-blocking activity. Carvedilol is a racemic mixture having the following structural formula:

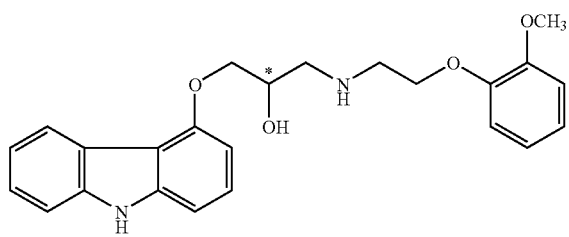

Carvedilol (I)

Carvedilol is the active ingredient of COREG®, which is indicated for the treatment of congestive heart failure and for the management of hypertension. Since carvedilol is a multiple-action drug, its beta-blocking activity affects the response to certain nerve impulses in parts of the body. As a result, beta-blockers decrease the heart's need for blood and oxygen by reducing its workload. Carvedilol is also known to be a vasodilator resulting primarily from alpha-adrenoceptor blockade. The multiple actions of carvedilol are responsible for the antihypertensive efficacy of the drug and for its effectiveness in managing congestive heart failure.

International Application No. WO 99/05105 (the '105 application) discloses that carvedilol can be isolated in two polymorphic forms, depending on the method of preparation. The two polymorphic forms, designated Form I and Form II, are reported to be monotropic and are distinguishable by their infrared, Raman and powder X-ray diffraction (PXRD) spectra. No evidence is found in the literature about the existence of solvate forms of carvedilol.

In Example 1 of the '105 application, Form I was generated by dissolving crude carvedilol in methanol, heating the solution, cooling the solution, and stirring the solution for a time sufficient to produce Form I. Form II was generated by recrystallizing Form I in 2-propanol.

The present invention relates to the solid state physical properties of carvedilol. These properties can be influenced by controlling the conditions under which carvedilol is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetric (DSC) and can be used to distinguish some polymorphic forms from others. A particular polymorphic form may also give rise to distinct spectroscopic properties that may be detectable by powder X-ray crystallography, solid state $^{13}C$ NMR spectrometry and infrared spectrometry.

The present invention also relates to solvates of carvedilol. When a substance crystallizes out of solution, it may trap molecules of solvent at regular intervals in the crystal lattice. Solvation also affects utilitarian physical properties of the solid state like flowability and dissolution rate.

One of the most important physical properties of a pharmaceutical compound, which can form polymorphs or solvates, is its solubility in aqueous solution, particularly the solubility in gastric juices of a patient. Other important properties relate to the ease of processing the form into pharmaceutical dosages, such as the tendency of a powdered or granulated form to flow and the surface properties that determine whether crystals of the form will adhere to each other when compacted into a tablet.

The discovery of new polymorphic forms and solvates of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. A new polymorphic form and solvate of carvedilol has been discovered.

SUMMARY OF THE INVENTION

In one aspect, the present invention provides a crystalline solid of carvedilol or a solvate thereof characterized by data selected from the group consisting of a PXRD pattern with peaks at about 6.5, 7.3, 16.0, and 30.5±0.2 degrees two-theta, a PXRD pattern with peaks at about 5.8, 10.7, 11.1, 11.5, 13.1, 13.7, 16.8, 17.7, 18.5, and 23.0±0.2 degrees two-theta, a DSC thermogram with endothermic peaks at about 74° C. and 112° C., and a FTIR spectrum with peaks at about 613, 740, 994, 1125, 1228, 1257, 1441, 1508, 1737, 2840, 3281, 3389, and 3470 cm$^{-1}$. Said solid crystalline form denotes Form VI.

In another aspect, the present invention provides a process for preparing a crystalline solid of carvedilol or a solvate thereof having at least one characteristic of Form VI (such as the PXRD peaks and/or FTIR peaks, and/or DSC peaks disclosed herein). In accordance with the process, carvedilol is contacted with ethyl acetate to form a solution. The solution is cooled and optionally seeded with carvedilol Form II. The solution can be stirred under high velocity agitation to form a suspension, which then can be cooled under high velocity agitation.

In yet another aspect, the present invention provides a process for preparing a crystalline solid of carvedilol Form II, including the steps of heating crystalline carvedilol having at least one characteristic of Form VI until the crystalline carvedilol is dry, mixing carvedilol Form II with the dry crystalline carvedilol, and storing the mixture for a holding time sufficient to transform the dry crystalline carvedilol into Form II.

DETAILED DESCRIPTION OF THE INVENTION

Figure 1:
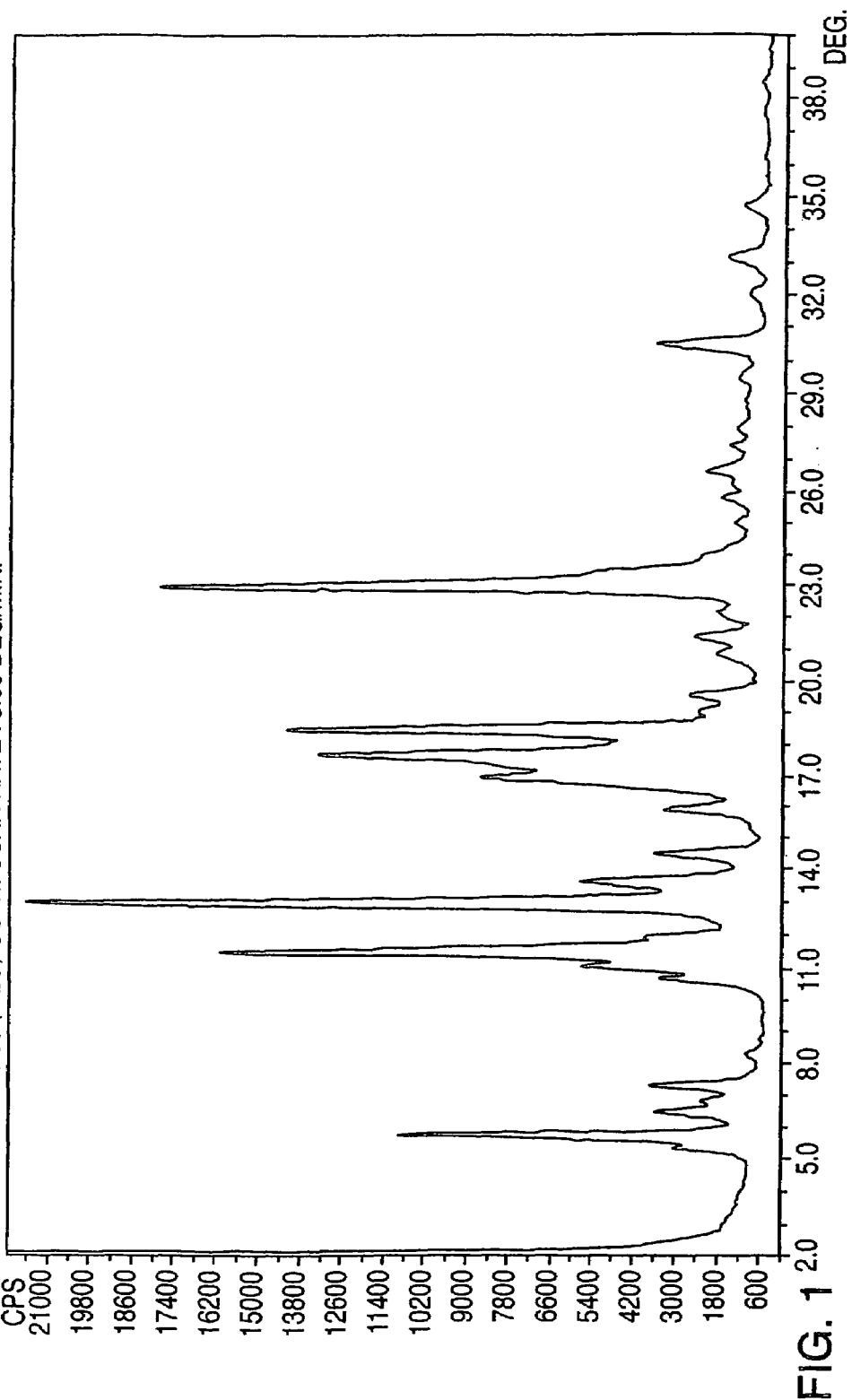
FIG. 1 is a PXRD pattern for carvedilol Form VI.

In one aspect, the present invention provides a novel crystalline solid of carvedilol or a solvate thereof, designated Form VI. Carvedilol solvate Form VI is characterized by a PXRD pattern (FIG. 1) with peaks at about 6.5, 7.3, 16.0, and 30.5±0.2 degrees two-theta. Further PXRD peaks were observed at about 5.8, 10.7, 11.1, 11.5, 13.1, 13.7, 16.8, 17.7, 18.5, and 23.0±0.2 degrees two-theta.

Figure 2:
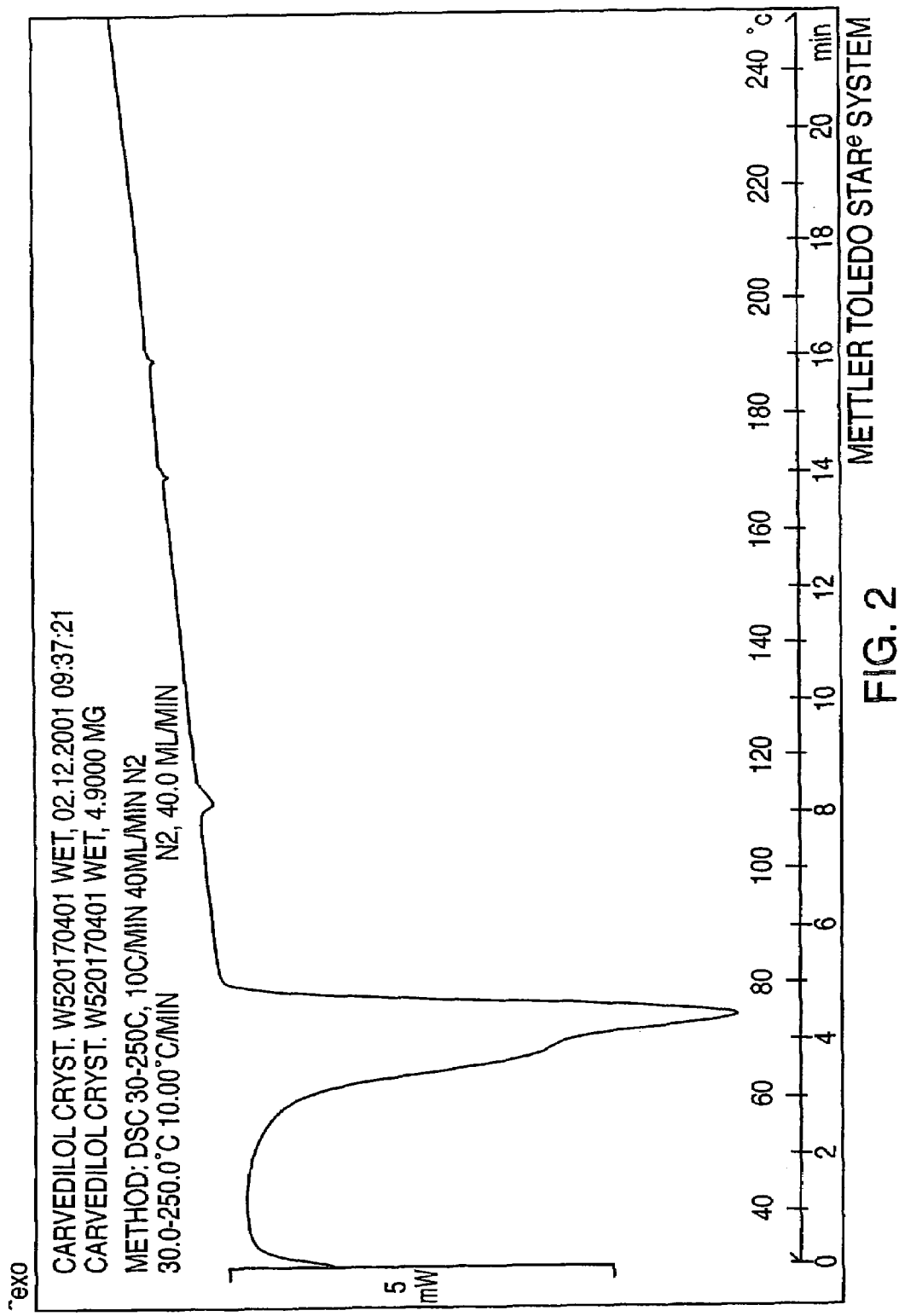
FIG. 2 is a FTIR spectrum for carvedilol Form VI.

Carvedilol solvate Form VI produces a FTIR spectrum (FIG. 2) with characteristic absorption bands at about 613, 740, 994, 1125, 1228, 1257, 1441, 1508, 1737, 2840, 3281, 3389, and 3470 cm$^{-1}$. Further FTIR peaks were observed at about 720, 1100, 1286, 1454, 1589, 2911, and 2935 cm$^{-1}$.

Figure 3:
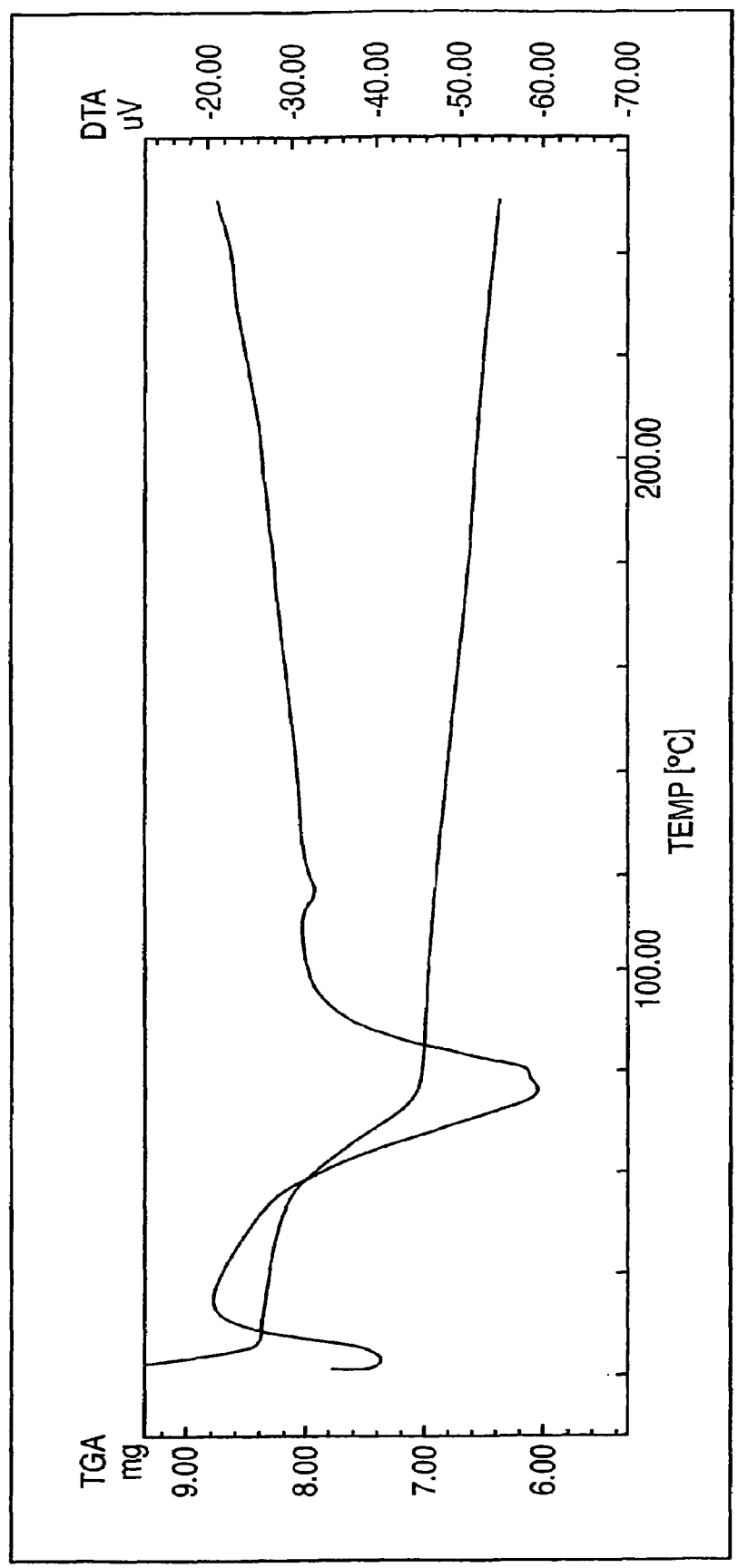
FIG. 3 is a DSC thermogram for carvedilol Form VI.

Carvedilol solvate Form VI produces a DSC thermogram (FIG. 3) showing two endothermic peaks: the main endothermic peak was observed at about 74° C. and a minor endotherm (dH=0.7 J/g) was observed at 112° C.

Figure 4:
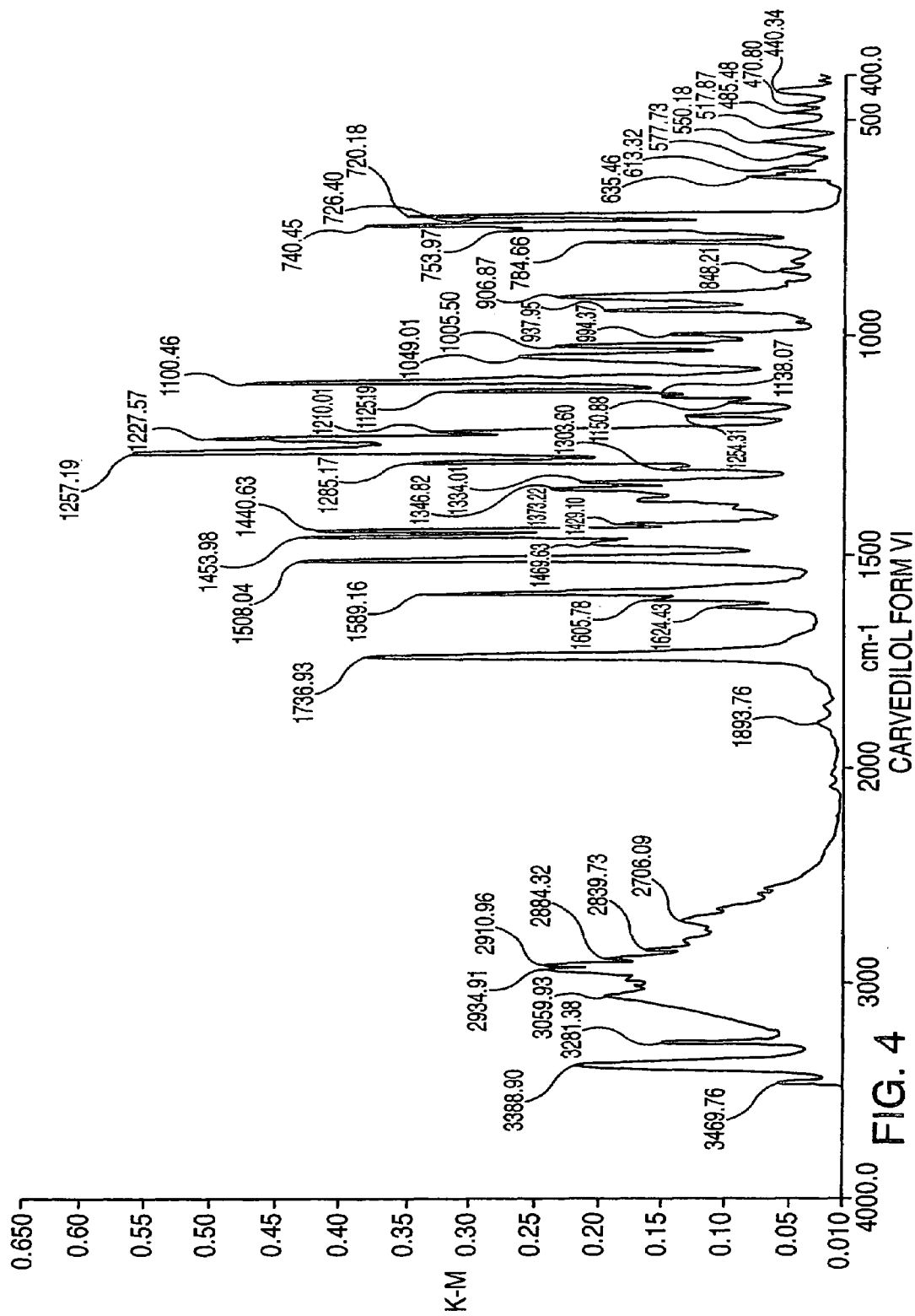
FIG. 4 is a DTG thermogram for carvedilol Form VI.

Carvedilol solvate Form VI produces a Differential Thermal Gravimetry (DTG) thermogram (FIG. 4) showing a weight loss step in the temperature range of 35-104° C. of about 13%. This value is equal to the expected value corresponding to two molecules of ethyl acetate per three molecules of carvedilol.

The water content of carvedilol solvate Form VI was tested by Karl-Fisher titration, which showed it to be free of water.

In another aspect, the present invention provides a novel process for preparing a crystalline solid of carvedilol or a solvate thereof, involving the steps of contacting carvedilol with ethyl acetate to form a solution, cooling the solution optionally under agitation. Preferably, the starting carvedilol is dry. The solution can optionally be seeded with carvedilol Form II. The solution can be stirred under high velocity agitation to form a suspension, which then can be cooled under high velocity agitation. The product obtained by this process has at least one characteristic of Form VI, and can be separated from the ethyl acetate by conventional means such as filtration. The product can also be dried.

Preferably, the mixture of ethyl acetate and dry carvedilol is heated to a temperature in the range of about 65° to about 80° C., most preferably in the range of about 70° to about 77° C. to form a solution. Thereafter, preferably, the temperature of the solution is reduced to between about 40° to about 55° C., most preferably between about 46° to about 50° C.

When the solution is seeded with carvedilol Form II, the seeded solution is stirred at a temperature in the range of about 46° C. to about 50° C. for a holding time sufficient to precipitate Form VI. A holding time of about 30 minutes under high velocity agitation (at least 260 rpm) is typically sufficient. Thereafter, the temperature of the suspension is preferably cooled to about 10° C. for a holding time, preferably about 3 hours under high velocity agitation. The cooled suspension should be stirred for about 30 minutes.

In another aspect, the present invention provides a process for preparing a crystalline solid of carvedilol Form II, including the steps of heating crystalline carvedilol having at least one characteristic of Form VI until the crystalline carvedilol is dry, mixing carvedilol Form II with the dry crystalline carvedilol, and storing the mixture for a holding time sufficient to transform the dry crystalline carvedilol into Form II.

Preferably, crystalline carvedilol having at least one characteristic of Form VI is heated to a temperate in the range of about 50° to about 60° C., and most preferably to about 55° C. The heating step can be preformed at atmospheric pressure or under reduced pressure. Preferably, the pressure is about 60 mm Hg, and more preferably about 30 mm Hg. Crystalline carvedilol having at least one characteristic of Form VI is typically dry after about 16 hours of heating.

Dry crystalline carvedilol having at least one characteristic of Form VI is mixed with carvedilol Form II and stored for a holding time sufficient to transform the dry crystalline carvedilol into Form II. A holding time of from about 1 week to about 2 weeks is typically sufficient. Carvedilol Form I can also be present.

Carvedilol Form VI can be milled into a powder and used in a pharmaceutical product or physically modified such as by granulation to produce larger granules of carvedilol Form VI. Carvedilol Form VI can also be used to prepare a liquid pharmaceutical product by dissolving or dispersing it in a liquid medium such as water, glycerin, vegetable oil and the like as discussed in greater detail below.

Carvedilol Form VI is useful for treating patients with congestive heart failure and hypertension and for producing a hypotensive effect in mammals, including human patients. Carvedilol Form VI can be formulated into a variety of compositions for administration to humans and mammals.

Pharmaceutical compositions of the present invention contain carvedilol Form VI, optionally in mixture with other crystalline forms and/or other active ingredients such as hydrochlorothiazide. In addition to the active ingredient(s), the pharmaceutical compositions of the present invention can contain one or more excipients. Excipients are added to the composition for a variety of purposes.

Diluents increase the bulk of a solid pharmaceutical composition and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flow properties of non-compacted solid composition and improve the accuracy of dosing. Excipients that can function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product form the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, carvedilol Form VI and any other solid excipients are dissolved or suspended in a liquid carrier such as water, vegetable oil, alcohol, polyethylene glycol, propylene glycol or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain a viscosity-enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste.

Preservatives and chelating agents such as alcohol, sodium benzoate, butylated hydroxy toluene, butylated hydroxyanisole and ethylenediamine tetraacetic acid can be added at levels safe for ingestion to improve storage stability.

A liquid composition according to the present invention can also contain a buffer such as guconic acid, lactic acid, citric acid or acetic acid, sodium guconate, sodium lactate, sodium citrate or sodium acetate.

Selection of excipients and the amounts to use can be readily determined by the formulation scientist based upon experience and consideration of standard procedures and reference works in the field.

The solid compositions of the present invention include powders, granulates, aggregates and compacted compositions.

Carvedilol Form VI can be administered for treatment of congestive heart failure and hypertension by any means that delivers the active ingredient(s) to the site of the body where beta-blocking activity exerts a therapeutic effect on the patient. For example, administration can be oral, buccal, parenteral (including subcutaneous, intramuscular, and intravenous) rectal, inhalant and ophthalmic. Although the most suitable route in any given case will depend on the nature and severity of the condition being treated, the most preferred route of the present invention is oral. Carvedilol Form VI can be conveniently administered to a patient in oral unit dosage form and prepared by any of the methods well-known in the pharmaceutical arts. Dosage forms include solid dosage forms like tablets, powders, capsules, sachets, troches and lozenges as well as liquid syrups, suspensions and elixirs.

The active ingredient(s) and excipients can be formulated into compositions and dosage forms according to methods known in the art.

A composition for tableting or capsule filing can be prepared by wet granulation. In wet granulation some or all of the active ingredients and excipients in powder form are blended and then further mixed in the presence of a liquid, typically water, that causes the powders to clump up into granules. The granulate is screened and/or milled, dried and then screened and/or milled to the desired particle size. The granulate can then be tableted or other excipients can be added prior to tableting such as a glidant and or lubricant.

A tableting composition can be prepared conventionally by dry blending. For instance, the blended composition of the actives and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

Yet more particularly, a tablet can, for example, be formulated by blending and directly compressing the composition in a tablet machine.

A capsule can, for example, be prepared by filling half of a gelatin capsule with the above tablet composition and capping it with the other half of the gelatin capsule.

A simple parenteral solution for injection can, for example, be prepared by combining carvedilol Form VI, sterile propylene glycol, and sterile water and sealing the composition in a sterile vial under sterile conditions.

Capsules, tablets and lozenges and other unit dosage forms preferably contain a dosage level of about 1 mg to about 100 mg of carvedilol Form VI.

The following examples are given for the purpose of illustrating the present invention and shall not be construed as limiting the scope or spirit of the invention.

EXAMPLES

General

The powder X-ray diffraction patterns were obtained by methods known in the art using a SCINTAG powder X-ray diffractometer model X'TRA, variable goniometer, equipped with a solid-state detector. Copper radiation of $\lambda=1.5418$ Å was used. The scanning parameters included: measurement range: 2-40 degrees two-theta; continuous scan; rate: 3 degrees/minute.

The thermogravimetric curves were obtained by methods known in the art using a Mettler Toledo DSC821$^e$. The weight of the samples was about 3-5 mg. The temperature range was from about 30° C. to at least 250° C., at the rate of 10° C./minute.

The thermogravimetric curves, were also obtained by methods known in the art using a Shimadzu DTG-50. The temperature range was from about 30° C. to at least 250° C., at the rate of 10° C./minute. Samples were purged with nitrogen gas at a flow rate of 20 ml/min.

The FTIR spectra were obtained by methods known in the art, such as diffuse reflectance, using a Perkin-Elmer, Spectrum One FTIR Spectrometer. The scanning parameters were as follows: range: 4000-400 cm$^{-1}$, 16 scans, resolution: 4.0 cm$^{-1}$.

Example 1

Carvedilol Form VI

Dry carvedilol (7 Kg) was added to ethyl acetate (70 L) and heated to about 70-77° C. under agitation. After complete dissolution, the solution was cooled to about 46-50° C. under agitation. The solution was then seeded with carvedilol Form II and stirred at a temperature of about 46-50° C. for about 30 minutes under high velocity agitation (at least 260 rpm). The resulting suspension was cooled to a temperature of about 10° C. over a period of 3 hours under high velocity agitation. The suspension was stirred for an addition 30 minutes and then filtered to obtain carvedilol Form VI.

Example 2

Carvedilol Form II

Three trays containing carvedilol Form VI (1 Kg per tray) were inserted into a vacuum oven, heated to about 55° C. under vacuum of 30 mm Hg and dried for about 16 hours. Immediately after drying, the polymorphic content of the dried sample was a mixture of Form VI and Form II. After storage at room temperature for about 4 weeks, a mixture of Form I, Form II and Form VI were found.

What is claimed is:

1. A process for preparing a crystalline ethyl acetate solvate of carvedilol characterized by a PXRD pattern having peaks at about 5.8, 6.5, 7.3, 10.7, 11.1, 11.5, 13.1, 13.7, 16.0, 16.8, 17.7, 18.5, 23.0, and 30.5±0.2 degrees two-theta wherein the PXRD pattern is substantially as in FIG. 1, the process comprising the steps of:
   contacting carvedilol and ethyl acetate to form a solution, and
   cooling the solution whereby a precipitate is formed.

2. The process of claim 1 wherein the cooling step is performed under agitation.

3. The process of claim 1 wherein the temperature of the solution is reduced to about 40° C. to about 55° C.

4. The process of claim 1 further comprising the steps of:
   seeding the solution with carvedilol Form II to form a suspension, and
   cooling the suspension whereby a precipitate is formed.

5. The process of claim 4 wherein the temperature of the suspension is reduced to about 10° C.

6. The process of claim 5 wherein the cooling step is performed under agitation.

* * * * *